(12) United States Patent
Strassner et al.

(10) Patent No.: US 11,712,509 B2
(45) Date of Patent: Aug. 1, 2023

(54) SEAL ASSEMBLY FOR CIRCULAR STAPLING INSTRUMENT

(71) Applicant: Covidien LP, Mansfield, MA (US)

(72) Inventors: Haley Strassner, Hamden, CT (US); Charles R. Kollar, Washington, DC (US); Drew R. Seils, Guilford, CT (US); Justin Williams, Southbury, CT (US); Joseph Eisinger, Northford, CT (US)

(73) Assignee: Covidien LP, Mansfield, MA (US)

( * ) Notice: Subject to any disclaimer, the term of this patent is extended or adjusted under 35 U.S.C. 154(b) by 14 days.

(21) Appl. No.: 17/470,396

(22) Filed: Sep. 9, 2021

(65) Prior Publication Data

US 2022/0105258 A1 Apr. 7, 2022

Related U.S. Application Data

(60) Provisional application No. 63/087,132, filed on Oct. 2, 2020.

(51) Int. Cl.
| | |
|---|---|
| *A61M 3/00* | (2006.01) |
| *A61M 3/02* | (2006.01) |
| *A61B 5/00* | (2006.01) |
| *A61B 17/115* | (2006.01) |
| *A61B 17/00* | (2006.01) |

(52) U.S. Cl.
CPC ......... *A61M 3/0295* (2013.01); *A61B 5/4255* (2013.01); *A61B 17/1155* (2013.01); *A61B 2017/00486* (2013.01); *A61B 2217/007* (2013.01)

(58) Field of Classification Search
CPC ..... A61B 17/1155; A61B 2017/07257; A61M 3/0295
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

Extended European Search Report issued in corresponding European Application No. 21200053.3 dated Feb. 18, 2022, 10 pages.

(Continued)

*Primary Examiner* — Eyamindae C Jallow
(74) *Attorney, Agent, or Firm* — Carter, DeLuca & Farrell, LLP

(57) ABSTRACT

A circular stapling instrument includes an adapter assembly having a tubular body, a shell assembly disposed on a distal portion of the tubular body, and a seal assembly supported on the tubular body. The seal assembly includes an inflatable member disposed proximal of the shell assembly, wherein the inflatable member includes a first diameter when in a deflated condition and a second diameter when in an inflated condition, the second diameter being larger than the first diameter.

19 Claims, 5 Drawing Sheets

(56) References Cited

U.S. PATENT DOCUMENTS

| | | |
|---|---|---|
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |

(56) References Cited

U.S. PATENT DOCUMENTS

| | | |
|---|---|---|
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |

(56) References Cited

U.S. PATENT DOCUMENTS

| | | | |
|---|---|---|---|
| 7,918,377 | B2 | 4/2011 | Measamer et al. |
| 7,922,062 | B2 | 4/2011 | Cole et al. |
| 7,922,742 | B2 | 4/2011 | Hillstead et al. |
| 7,922,743 | B2 | 4/2011 | Heinrich et al. |
| 7,931,183 | B2 | 4/2011 | Orban, III |
| 7,938,307 | B2 | 5/2011 | Bettuchi |
| 7,942,302 | B2 | 5/2011 | Roby et al. |
| 7,951,166 | B2 | 5/2011 | Orban, III et al. |
| 7,959,050 | B2 | 6/2011 | Smith et al. |
| 7,967,181 | B2 | 6/2011 | Viola et al. |
| 7,975,895 | B2 | 7/2011 | Milliman |
| 8,002,795 | B2 | 8/2011 | Beetel |
| 8,006,701 | B2 | 8/2011 | Bilotti et al. |
| 8,006,889 | B2 | 8/2011 | Adams et al. |
| 8,011,551 | B2 | 9/2011 | Marczyk et al. |
| 8,011,554 | B2 | 9/2011 | Milliman |
| 8,016,177 | B2 | 9/2011 | Bettuchi et al. |
| 8,016,858 | B2 | 9/2011 | Whitman |
| 8,020,741 | B2 | 9/2011 | Cole et al. |
| 8,025,199 | B2 | 9/2011 | Whitman et al. |
| 8,028,885 | B2 | 10/2011 | Smith et al. |
| 8,038,046 | B2 | 10/2011 | Smith et al. |
| 8,043,207 | B2 | 10/2011 | Adams |
| 8,066,167 | B2 | 11/2011 | Measamer et al. |
| 8,066,169 | B2 | 11/2011 | Viola |
| 8,070,035 | B2 | 12/2011 | Holsten et al. |
| 8,070,037 | B2 | 12/2011 | Csiky |
| 8,096,458 | B2 | 1/2012 | Hessler |
| 8,109,426 | B2 | 2/2012 | Milliman et al. |
| 8,109,427 | B2 | 2/2012 | Orban, III |
| 8,113,405 | B2 | 2/2012 | Milliman |
| 8,113,406 | B2 | 2/2012 | Holsten et al. |
| 8,113,407 | B2 | 2/2012 | Holsten et al. |
| 8,123,103 | B2 | 2/2012 | Milliman |
| 8,128,645 | B2 | 3/2012 | Sonnenschein et al. |
| 8,132,703 | B2 | 3/2012 | Milliman et al. |
| 8,136,712 | B2 | 3/2012 | Zingman |
| 8,146,790 | B2 | 4/2012 | Milliman |
| 8,146,791 | B2 | 4/2012 | Bettuchi et al. |
| 8,181,838 | B2 | 5/2012 | Milliman et al. |
| 8,192,460 | B2 | 6/2012 | Orban, III et al. |
| 8,201,720 | B2 | 6/2012 | Hessler |
| 8,203,782 | B2 | 6/2012 | Brueck et al. |
| 8,211,130 | B2 | 7/2012 | Viola |
| 8,225,799 | B2 | 7/2012 | Bettuchi |
| 8,225,981 | B2 | 7/2012 | Criscuolo et al. |
| 8,231,041 | B2 | 7/2012 | Marczyk et al. |
| 8,231,042 | B2 | 7/2012 | Hessler et al. |
| 8,257,391 | B2 | 9/2012 | Orban, III et al. |
| 8,267,301 | B2 | 9/2012 | Milliman et al. |
| 8,272,552 | B2 | 9/2012 | Holsten et al. |
| 8,276,802 | B2 | 10/2012 | Kostrzewski |
| 8,281,975 | B2 | 10/2012 | Criscuolo et al. |
| 8,286,845 | B2 | 10/2012 | Perry et al. |
| 8,308,045 | B2 | 11/2012 | Bettuchi et al. |
| 8,312,885 | B2 | 11/2012 | Bettuchi et al. |
| 8,313,014 | B2 | 11/2012 | Bettuchi |
| 8,317,073 | B2 | 11/2012 | Milliman et al. |
| 8,317,074 | B2 | 11/2012 | Ortiz et al. |
| 8,322,590 | B2 | 12/2012 | Patel et al. |
| 8,328,060 | B2 | 12/2012 | Jankowski et al. |
| 8,328,062 | B2 | 12/2012 | Viola |
| 8,328,063 | B2 | 12/2012 | Milliman et al. |
| 8,343,185 | B2 | 1/2013 | Milliman et al. |
| 8,353,438 | B2 | 1/2013 | Baxter, III et al. |
| 8,353,439 | B2 | 1/2013 | Baxter, III et al. |
| 8,353,930 | B2 | 1/2013 | Heinrich et al. |
| 8,360,295 | B2 | 1/2013 | Milliman et al. |
| 8,365,974 | B2 | 2/2013 | Milliman |
| 8,403,942 | B2 | 3/2013 | Milliman et al. |
| 8,408,441 | B2 | 4/2013 | Wenchell et al. |
| 8,413,870 | B2 | 4/2013 | Pastorelli et al. |
| 8,413,872 | B2 | 4/2013 | Patel |
| 8,418,905 | B2 | 4/2013 | Milliman |
| 8,418,909 | B2 | 4/2013 | Kostrzewski |
| 8,424,535 | B2 | 4/2013 | Hessler et al. |
| 8,424,741 | B2 | 4/2013 | McGuckin, Jr. et al. |
| 8,430,291 | B2 | 4/2013 | Heinrich et al. |
| 8,430,292 | B2 | 4/2013 | Patel et al. |
| 8,453,910 | B2 | 6/2013 | Bettuchi et al. |
| 8,453,911 | B2 | 6/2013 | Milliman et al. |
| 8,479,968 | B2 | 7/2013 | Hodgkinson et al. |
| 8,485,414 | B2 | 7/2013 | Criscuolo et al. |
| 8,490,853 | B2 | 7/2013 | Criscuolo et al. |
| 8,511,533 | B2 | 8/2013 | Viola et al. |
| 8,551,138 | B2 | 10/2013 | Orban, III et al. |
| 8,567,655 | B2 | 10/2013 | Nalagatla et al. |
| 8,579,178 | B2 | 11/2013 | Holsten et al. |
| 8,590,763 | B2 | 11/2013 | Milliman |
| 8,590,764 | B2 | 11/2013 | Hartwick et al. |
| 8,608,047 | B2 | 12/2013 | Holsten et al. |
| 8,616,428 | B2 | 12/2013 | Milliman et al. |
| 8,616,429 | B2 | 12/2013 | Viola |
| 8,622,275 | B2 | 1/2014 | Baxter, III et al. |
| 8,627,995 | B2 | 1/2014 | Smith et al. |
| 8,631,993 | B2 | 1/2014 | Kostrzewski |
| 8,636,187 | B2 | 1/2014 | Hueil et al. |
| 8,640,940 | B2 | 2/2014 | Ohdaira |
| 8,646,674 | B2 | 2/2014 | Schulte et al. |
| 8,662,370 | B2 | 3/2014 | Takei |
| 8,663,258 | B2 | 3/2014 | Bettuchi et al. |
| 8,672,207 | B2 | 3/2014 | Shelton, IV et al. |
| 8,672,931 | B2 | 3/2014 | Goldboss et al. |
| 8,672,951 | B2 | 3/2014 | Smith et al. |
| 8,678,264 | B2 | 3/2014 | Racenet et al. |
| 8,679,137 | B2 | 3/2014 | Bauman et al. |
| 8,684,248 | B2 | 4/2014 | Milliman |
| 8,684,250 | B2 | 4/2014 | Bettuchi et al. |
| 8,684,251 | B2 | 4/2014 | Rebuffat et al. |
| 8,684,252 | B2 | 4/2014 | Patel et al. |
| 8,695,864 | B1 | 4/2014 | Hausen |
| 8,708,212 | B2 | 4/2014 | Williams |
| 8,733,611 | B2 | 5/2014 | Milliman |
| 8,733,615 | B2 | 5/2014 | Nalagatla et al. |
| 8,746,531 | B2 | 6/2014 | Wenchell et al. |
| 8,746,532 | B2 | 6/2014 | Nalagatla et al. |
| 8,783,543 | B2 | 7/2014 | Shelton, IV et al. |
| 8,789,737 | B2 | 7/2014 | Hodgkinson et al. |
| 8,800,838 | B2 | 8/2014 | Shelton, IV |
| 8,800,841 | B2 | 8/2014 | Ellerhorst et al. |
| 8,801,734 | B2 | 8/2014 | Shelton, IV et al. |
| 8,801,735 | B2 | 8/2014 | Shelton, IV et al. |
| 8,821,523 | B2 | 9/2014 | Heinrich et al. |
| 8,827,903 | B2 | 9/2014 | Shelton, IV et al. |
| 8,833,629 | B2 | 9/2014 | Nalagatla et al. |
| 8,840,004 | B2 | 9/2014 | Holsten et al. |
| 8,844,792 | B2 | 9/2014 | Viola |
| 8,845,661 | B2 | 9/2014 | D'Arcangelo et al. |
| 8,870,911 | B2 | 10/2014 | Williams et al. |
| 8,875,974 | B2 | 11/2014 | Rebuffat et al. |
| 8,893,948 | B2 | 11/2014 | Williams |
| 8,910,847 | B2 | 12/2014 | Nalagatla et al. |
| 8,925,785 | B2 | 1/2015 | Holsten et al. |
| 8,925,786 | B2 | 1/2015 | Holsten et al. |
| 8,967,448 | B2 | 3/2015 | Carter et al. |
| 8,978,955 | B2 | 3/2015 | Aronhalt et al. |
| 9,010,608 | B2 | 4/2015 | Casasanta, Jr. et al. |
| 9,010,612 | B2 | 4/2015 | Stevenson et al. |
| 9,016,540 | B2 | 4/2015 | Whitman et al. |
| 9,033,204 | B2 | 5/2015 | Shelton, IV et al. |
| 9,095,340 | B2 | 8/2015 | Felder et al. |
| 9,113,871 | B2 | 8/2015 | Milliman et al. |
| 9,113,877 | B1 | 8/2015 | Whitman et al. |
| 9,113,883 | B2 | 8/2015 | Aronhalt et al. |
| 9,113,884 | B2 | 8/2015 | Shelton, IV et al. |
| 9,113,885 | B2 | 8/2015 | Hodgkinson et al. |
| 9,125,654 | B2 | 9/2015 | Aronhalt et al. |
| 9,155,536 | B1 | 10/2015 | Hausen et al. |
| 9,161,757 | B2 | 10/2015 | Bettuchi |
| 9,204,881 | B2 | 12/2015 | Penna |
| 9,211,122 | B2 | 12/2015 | Hagerty et al. |
| 9,220,504 | B2 | 12/2015 | Viola et al. |
| 9,232,941 | B2 | 1/2016 | Mandakolathur Vasudevan et al. |
| 9,232,945 | B2 | 1/2016 | Zingman |

(56) References Cited

U.S. PATENT DOCUMENTS

| | | |
|---|---|---|
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,130,368 B2 | 11/2018 | Matonick et al. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2011/0257667 A1 | 10/2011 | Nakamura et al. |
| 2012/0125972 A1* | 5/2012 | Holsten ............ A61B 17/07207 227/176.1 |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |

(56) References Cited

U.S. PATENT DOCUMENTS

| | | | |
|---|---|---|---|
| 2014/0046352 A1 | 2/2014 | Reboa et al. | |
| 2014/0158747 A1 | 6/2014 | Measamer et al. | |
| 2014/0284370 A1 | 9/2014 | Sahin | |
| 2015/0083772 A1 | 3/2015 | Miller et al. | |
| 2015/0173763 A1 | 6/2015 | Liu | |
| 2015/0209045 A1 | 7/2015 | Hodgkinson et al. | |
| 2019/0175888 A1* | 6/2019 | Abdelwahed | A61M 29/02 |
| 2019/0357934 A1* | 11/2019 | Borek | A61B 1/313 |
| 2020/0108238 A1* | 4/2020 | Matlock | A61B 90/08 |
| 2020/0376187 A1* | 12/2020 | Walcott | A61D 7/00 |
| 2020/0397976 A1* | 12/2020 | Rontal | A61M 1/77 |
| 2021/0338056 A1* | 11/2021 | Nakajima | A61B 17/12045 |
| 2021/0338920 A1* | 11/2021 | Nakajima | A61B 1/2736 |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1671597 A1 | 6/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3023077 A1 | 5/2016 |
| EP | 3412225 A1 | 12/2018 |
| EP | 3549545 A2 | 10/2019 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9835614 A1 | 8/1998 |
| WO | 0154594 A1 | 8/2001 |
| WO | 02080781 A2 | 10/2002 |
| WO | 2004047654 A2 | 6/2004 |
| WO | 2008107918 A1 | 9/2008 |
| WO | 2019130087 A1 | 7/2019 |

OTHER PUBLICATIONS

Extended European Search Report from Appl. No. 14181908.6 dated May 26, 2015.

European Examination Report from Appl. No. 14181908.6 dated May 3, 2016.

\* cited by examiner

SEAL ASSEMBLY FOR CIRCULAR STAPLING INSTRUMENT

CROSS-REFERENCE TO RELATED APPLICATION

This application claims the benefit of and prior to U.S. Provisional Patent Application No. 63/087,132, filed on Oct. 2, 2020, the content of which is incorporated herein by reference in its entirety.

FIELD

The disclosure relates to circular stapling instruments with irrigation catheters. More particularly, the disclosure relates to seal assemblies for use with circular stapling instruments having irrigation catheters.

BACKGROUND

Circular stapling instruments may be used in endoscopic procedures, laparoscopic procedures, or through natural body orifices, for fastening tissue. The circular stapling instruments may be powered or manually-operated and may include a tool assembly that is configured to operably couple to a distal end of an elongated member that extends from a handle assembly, e.g., adapter assembly. The handle assembly may be reusable and the tool assembly may be disposable. The tool assembly may include an anvil assembly and a cartridge assembly that houses one or more fasteners therein.

In use, a circular stapling instrument (or circular surgical staplers) may be used to reattach rectum portions that were previously transected. In this instance, a physician may insert a distal end (including an anvil assembly) of the circular stapling instrument into a rectum of a patient and maneuver the distal end up the colonic tract of the patient toward the transected rectum portions. The physician may also insert the remainder of the circular stapling instrument (including the cartridge assembly) through an incision and toward the transected rectum portions. The anvil and cartridge assemblies are approximated toward one another and staples are ejected from the cartridge assembly toward the anvil assembly to form the staples in tissue to affect an end-to-end anastomosis.

After the end-to-end anastomosis is formed, and before the circular stapling instrument is removed from the surgical site, an irrigation catheter or other accessory may be used to leak test the anastomosis. When pressure testing the anastomosis, some amount of pressure is lost due to a lack of seal around the anus.

Therefore, it may be beneficial to provide a seal assembly for circular stapling instruments that aids in forming a seal between the circular stapling instrument and the patient.

SUMMARY

A circular stapling instrument includes an adapter assembly including a tubular body, a shell assembly disposed on a distal portion of the tubular body, and a seal assembly supported on the tubular body. The seal assembly includes an inflatable member disposed proximal of the shell assembly. The inflatable member includes a first diameter when the inflatable member is in a deflated condition and a second diameter when the inflatable member is in an inflated condition. The second diameter is larger than the first diameter.

In certain aspects of the disclosure, the circular stapling instrument further includes an irrigation assembly. The irrigation assembly may include a flexible tube. The inflatable member may be received about the flexible tube of the irrigation assembly.

In other aspects of the disclosure, the inflatable member is slidably disposed about the tubular body of the adapter assembly when in the deflated condition. The shell assembly may include a cross-section having a third diameter. The third diameter may be greater than the first diameter. The second diameter may be greater than the third diameter. The seal assembly may further include an inflation tube for providing fluid to the inflatable member. The inflatable member may be substantially annular. The inflatable member may be an inflatable cuff or an inflatable sleeve.

A method of sealing a tubular body organ following a stapling procedure to perform a leak test includes inserting a distal portion of a shell assembly of the circular stapling instrument into an entrance to the tubular body organ, performing a stapling procedure, and inflating an inflatable member proximal of the shell assembly to create a seal between the distal portion of the circular stapling instrument and the tubular body organ.

BRIEF DESCRIPTION OF THE DRAWINGS

The above and other aspects, features, and advantages of this disclosure will be apparent in light of the following detailed description when taken in conjunction with the accompanying drawings, which are incorporated in and constitute a part of this specification, wherein.

DETAILED DESCRIPTION

Figure 1:
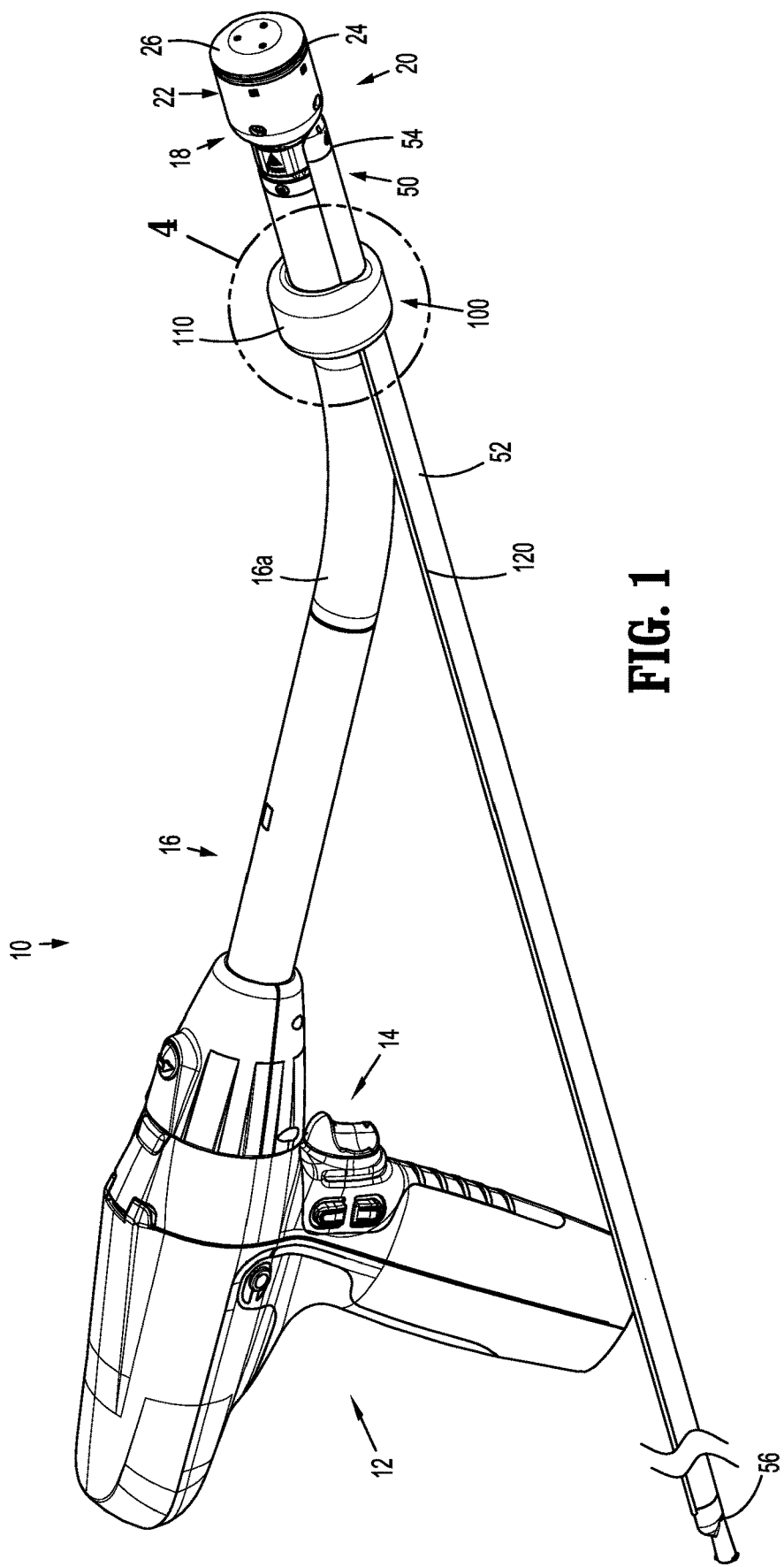
FIG. 1 is a perspective view of a circular stapling instrument including an irrigation assembly and a seal assembly, in accordance with aspects of the disclosure.

Aspects of this disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. Directional reference terms, such as "top," "bottom," "side," and the like, are used to ease description of the aspects and are not intended to have any limiting effect on the ultimate orientation of a structure or any part thereof. In the following description, well-known functions or constructions are not described in detail to avoid obscuring this disclosure in unnecessary detail.

FIG. 1 illustrates a powered circular stapling instrument 10 in accordance with aspects of the disclosure. Generally, circular stapling instrument 10 includes a housing or handle assembly 12 having an actuator 14, and an adapter assembly 16 extending distally from and releasably secured to the handle assembly 12. As shown, the adapter assembly 16 includes a curved tubular body 16a. However, it is envisioned that tubular body 16a of the adapter assembly 16 may be linear to suit a particular surgical procedure, e.g., mucosectomy, hemorrhoidectomy. A tool assembly 18 (e.g., a multi-use loading unit, or a single-use loading unit) is coupled to or is configured to operably couple to a distal end of the adapter assembly 16 and includes an end effector 20. In certain aspects of the disclosure, a proximal portion of the tool assembly 18 is formed as a single component with the adapter assembly 16. Although the aspects of the disclosure are shown and described with regards to a powered circular stapling instrument 10, it is envisioned that the aspects of the disclosure are equally applicable with manual circular stapling instruments.

The end effector 20 of the tool assembly 18 includes a shell assembly 22 configured to support a cartridge assembly 24. The cartridge assembly 24 supports a plurality of fasteners (not shown) and a corresponding plurality of pusher members (not shown) that are operatively engageable with the plurality of fasteners to eject the plurality of fasteners from the cartridge assembly 24.

The end effector 20 of the tool assembly 18 also includes an anvil assembly 26 that is supported to move in relation to the cartridge assembly 24 between spaced and approximated positions. The anvil assembly 26 includes a plurality of pockets or depressions (not shown) that are each configured to receive and form a fastener of the plurality of fasteners when the plurality of fasteners are deployed from cartridge assembly 24.

The adapter assembly 16 includes an irrigation/suction assembly 50 and a seal assembly 100. The irrigation assembly 50 is supported on a distal portion of the adapter assembly 16 and operably engages the shell assembly 22 of the tool assembly 18. More particularly, the irrigation assembly 50 includes a flexible tube 52, a distal coupling 54 secured to a distal portion of the flexible tube 52, and a proximal coupling 56 secured to a proximal portion of the flexible tube 52. The distal coupling 54 is configured to connect the flexible tube 52 with the shell assembly 22, and the proximal coupling 56 is configured to connect the flexible tube 52 with a source of irrigation fluid (not shown) and a source of suction (not shown). It is envisioned that the sources of irrigation fluid and suction may be the same.

In certain aspects of the disclosure, the distal coupling 54 of the irrigation assembly 50 is integrally formed with the shell assembly 22. Alternatively, the irrigation assembly 50 may form an accessory that is releasably securable to the adapter assembly 16 and/or the shell assembly 22.

The flexible tube 52 of the irrigation assembly 50 extends longitudinally at least partially along the tubular body 16a of the adapter assembly 16 (FIG. 1) and may be fixedly secured to a portion of the circular stapling instrument 10 (e.g., the shell assembly 22, the adapter assembly 16, and/or the handle assembly 12) via one or more suitable securement methods (e.g., low tack adhesives, clips, bands, press- or friction-fit, etc.), not explicitly shown. It is further envisioned that flexible tube 52 can be any reasonable length and may extend beyond the circular stapling instrument 10. Although shown as described as being flexible, it is envisioned that the flexible tube 52 may be rigid.

The irrigation assembly 50 is provided to pressure test the anastomosis following a stapling procedure. The irrigation assembly 50 may also be provided to facilitate in insertion of the end effector 20 into a tubular body of a patient. For a detailed description of the structure and function of exemplary irrigation assemblies, please refer to U.S. Pat. No. 10,561,422 (hereinafter, "the '422 patent"), the entire content of which is incorporated herein by reference.

Figure 2:
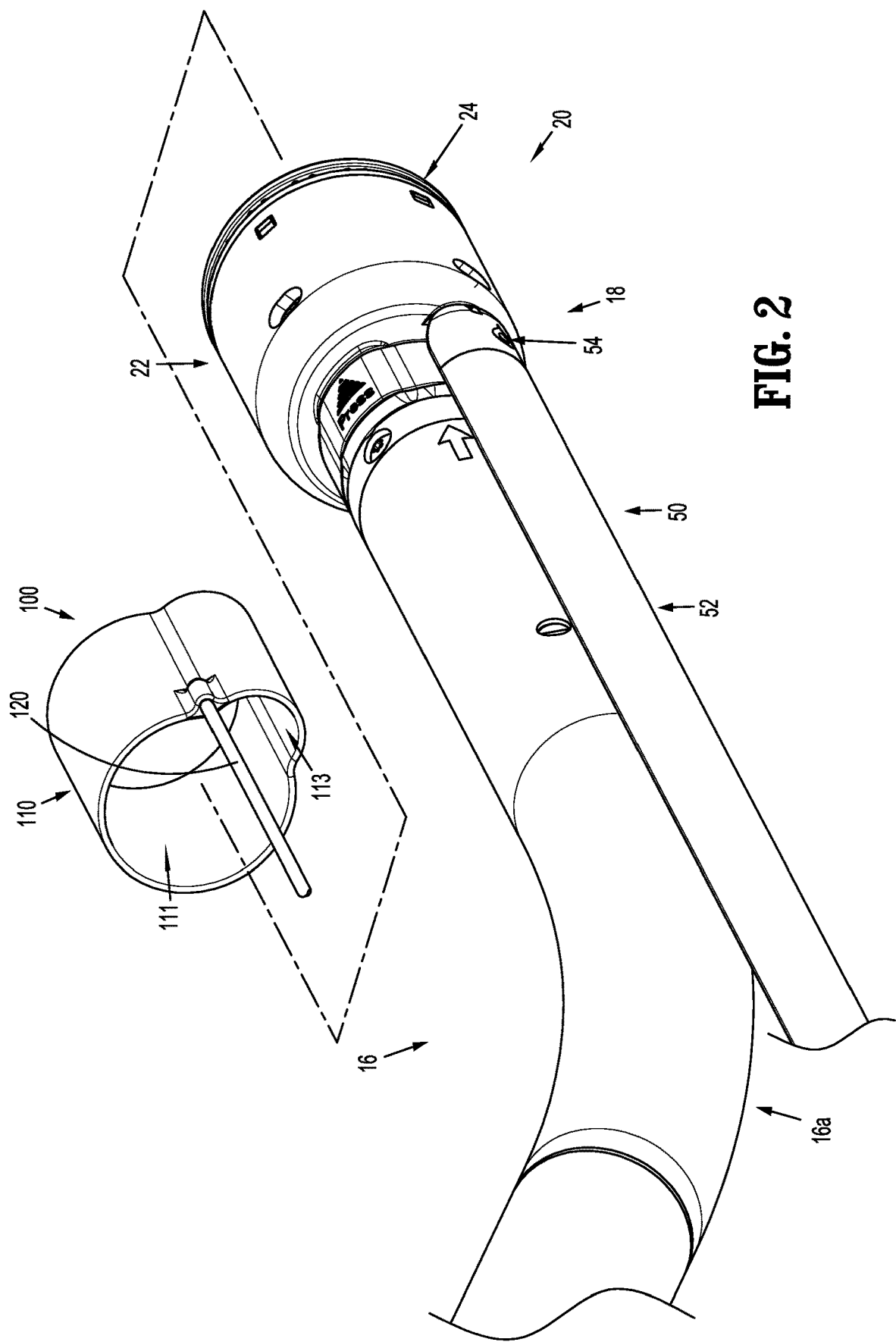
FIG. 2 is a perspective view of a distal portion of the circular stapling instrument and the seal assembly shown in FIG. 1.

FIG. 2 illustrates the seal assembly 100 separated from the adapter assembly 16. As shown, the seal assembly 100 defines an accessory that may be selectively secured to the adapter assembly 16 of the circular stapling instrument 10 (FIG. 1). Alternatively, the seal assembly 100 may be incorporated into either or both of the adapter assembly 16 and the irrigation assembly 50.

The seal assembly 100 includes an inflatable cuff 110 and an inflation tube 120 secured to the inflatable cuff 110. The inflatable cuff 110 is configured to be received about the tubular body 16a of the adapter assembly 16 and the flexible tube 52 of the irrigation assembly 50. It is envisioned that the inflatable cuff 110 may form a fluid tight seal with the tubular body 16a and the flexible tube 52 prior to inflation of the inflatable cuff 110.

In certain aspects of the disclosure, and as shown, to accommodate the tubular body 16a of the adapter assembly 16 and the flexible tube 52 of the irrigation assembly 50, and to ensure a fluid tight seal between the inflatable cuff 110 and the adapter assembly 16, the inflatable cuff 110 includes a central opening 111 sized to receive the tubular body 16a of the adapter assembly 16 and a channel 113 in fluid communication with the central opening 111 sized to receive the flexible tube 52 of the irrigation assembly 50. More particularly, the central opening 111 includes a substantially circular shape corresponding to a cross-sectional shape of the tubular body 16a and the channel 113 includes a substantially semicircular shape corresponding to a cross-sectional shape of the flexible tube 52. It is envisioned that central opening 111 may have any shape corresponding to alternative configurations of the tubular body 16a and the channel 113 may have any shape corresponding with alternative configurations of the flexible tube 52. When the seal assembly 100 is properly secured to the adapter assembly 16, the tubular body 16a is disposed within the central opening 111 of the inflatable cuff 110 and the flexible tube 52 is disposed within the channel 113 of the inflatable cuff 110.

The inflatable cuff 110 may be formed of any suitable material. Although shown as being formed from an elastic material that stretches between deflated and inflated conditions, it is envisioned that the inflatable cuff 110 may instead form a collapsible bag (not shown) which may be disposed in a tear-away cover. In other aspects of the disclosure, the inflatable cuff 110 is textured, coated, or otherwise configured to form a fluid tight seal between the inflatable cuff 110 and the tubular body 16a of the adapter assembly 16 and the flexible tube 52 of the irrigation assembly 50, e.g., inwardly, and/or between the inflatable cuff 110 and a tubular organ, e.g., anus "An" of a patient "P", e.g., outwardly. It is envisioned that the inflatable cuff 110 is moveable along the tubular body 16*a* of the adapter assembly 16 when the inflatable cuff 110 is in the deflated condition, and is fixed relative to the tubular body 16*a* when the inflatable cuff 110 is in the inflated condition.

A distal portion of the inflation tube 120 is secured to the inflatable cuff 110 in any suitable manner. It is envisioned that the inflation tube 120 may be incorporated into the flexible tube 52 and/or distal and proximal coupling 54, 56. A proximal portion of the inflation tube 120 is configured to be secured to a source of inflation fluid (not shown). It is envisioned that the inflatable cuff 110 may be inflated with liquid, e.g., saline, and/or gas, e.g., nitrogen. Inflation may occur manually, e.g., rubber bulb, or automatically, e.g., pressurized gas. The seal assembly 100 may include a valve (not shown) for selective release of the inflation fluid.

Figure 3:
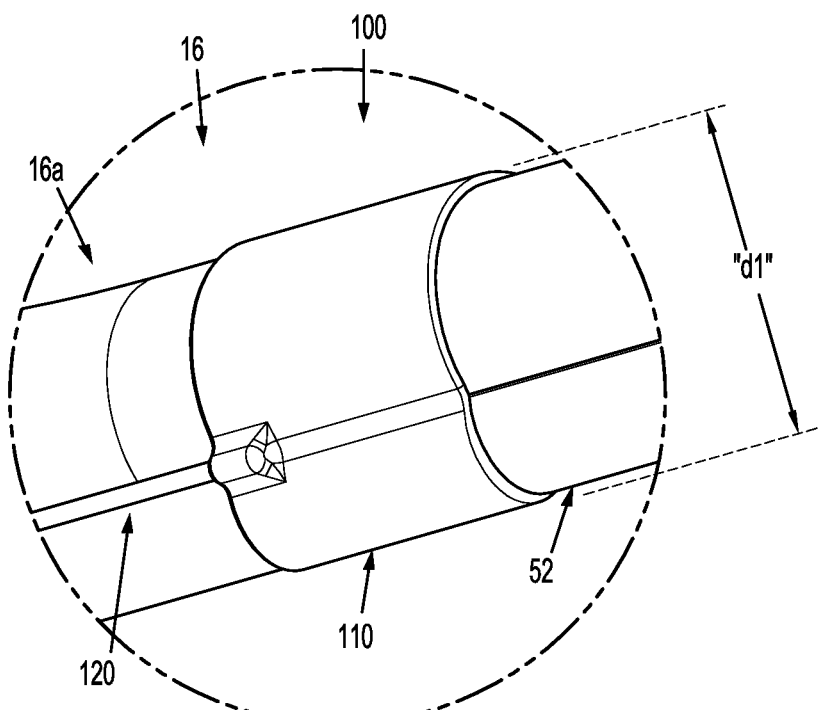
FIG. 3 is an enlarged view of the indicated area of detail shown in FIG. 1, with an inflatable cuff of the seal assembly shown in FIG. 1, in a deflated condition.

FIG. 3 illustrates the seal assembly 100 with the inflatable cuff 110 operably disposed about the tubular body 16*a* of the adapter assembly 16 and the flexible tube 52 of the irrigation assembly 50, and in a deflated condition. It is envisioned that the seal assembly 100 may be provided with the adapter assembly 16 or provided as a separate accessory. Alternatively, the seal assembly 100 may be integrally formed with the adapter assembly 16 and/or the irrigation assembly 50. When provided as a separate accessory, the seal assembly 100 may be received about the tubular body 16*a* of the adapter assembly 16 by stretching the inflatable cuff 110 like a rubber band and guiding it over the end effector 20. The location of the inflatable cuff 110 along the tubular body 16*a* of the adapter assembly 16 may be adjusted depending on the size of the patient "P", the procedure being performed.

In the deflated condition, an outer diameter of the inflatable cuff 110 measures a first length "d1". The first length "d1" is less that the length or dimension of the diameter of a cross-section of the shell assembly 22. In this manner, the inflatable cuff 110 is maintained within the diameter of the shell assembly 22 and does not require any further dilation of the tubular organ of the patient.

Figure 4:
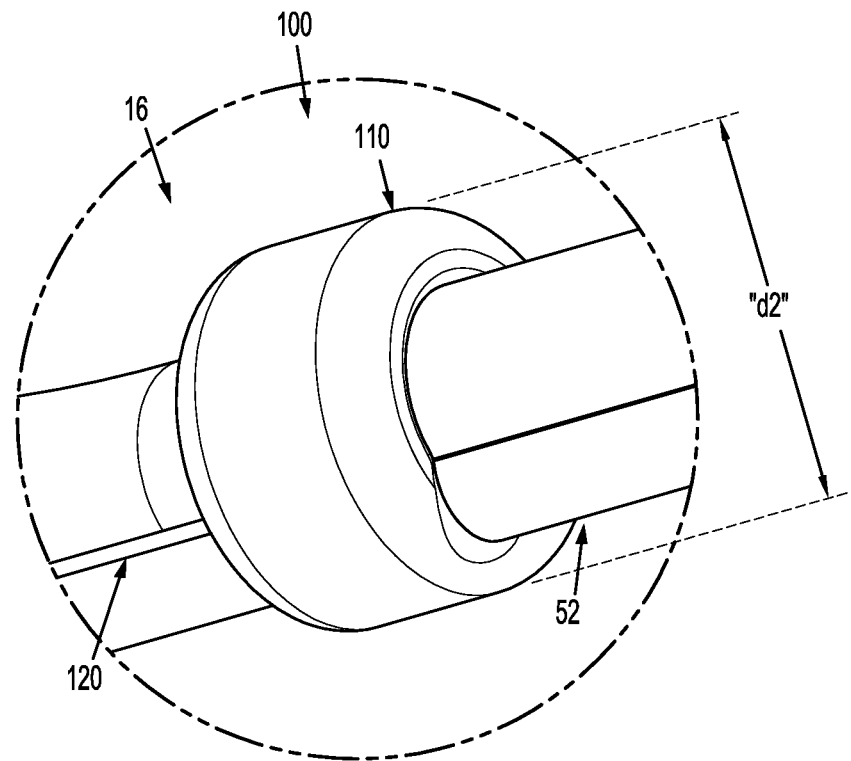
FIG. 4 is an enlarged view of the indicated area of detail shown in FIG. 1, with the inflatable cuff of the seal assembly shown in FIG. 1, in an inflated condition.

FIG. 4 illustrates the seal assembly 100 with the inflatable cuff 110 in an inflated condition. In the inflated condition, an outer diameter of the inflatable cuff 100 measures a second length "d2". The second length "d2" is greater than the first length "d1", and as shown, may be greater than the cross-sectional diameter of the shell assembly 22. The inflated inflatable cuff 110 includes an annular shape with rounded or smooth surfaces.

Figure 5:
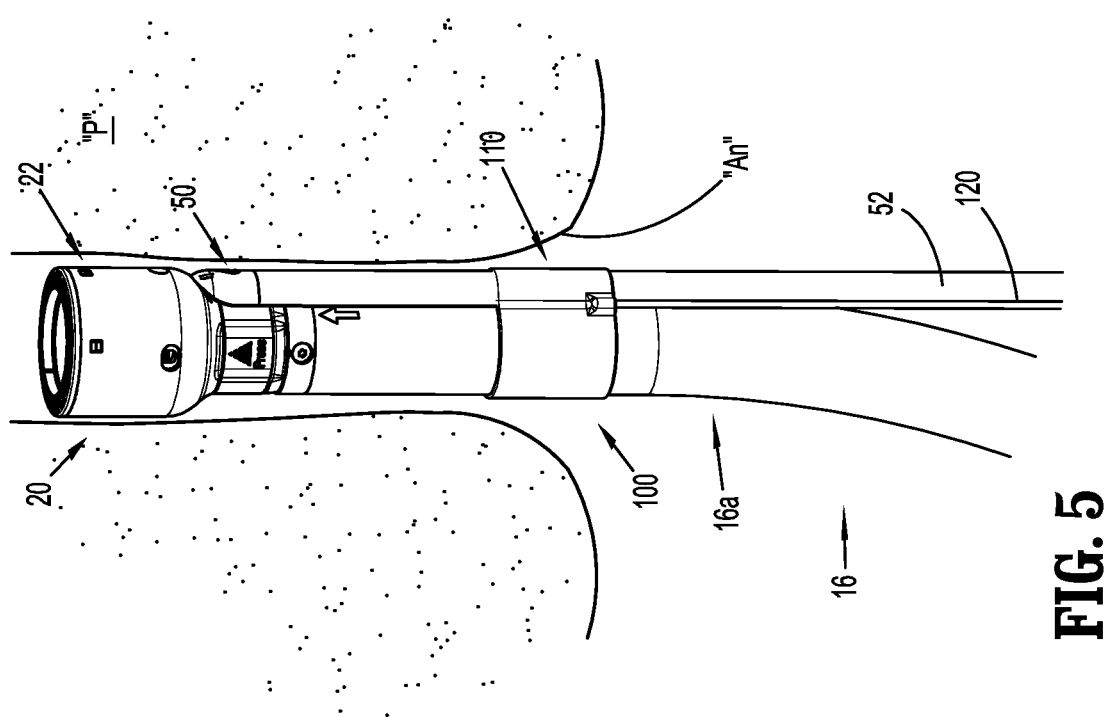
FIG. 5 is a side view of the distal portion of the circular stapling instrument shown in FIG. 1, including the seal assembly, received within an anus of a patient and with the inflatable cuff in its deflated condition.

FIG. 5 illustrates the end effector 20 of the circular stapling instrument 10, including the irrigation assembly 50 and seal assembly 100 received within a tubular organ, e.g., the anus "An" of a patient "P". The inflatable cuff 110 of the seal assembly 100 may be coated, include a cover, or be otherwise configured to facilitate positioning of the inflatable cuff 110 within the anus "An" of the patient "P". Depending on the position of the anastomosis and/or the size of the patient "P", the position of the inflatable cuff 110 on the tubular body 16 of the adapter assembly 16 may be adjusted. As shown, the inflatable cuff 110 is positioned along the tubular body 16 of the adapter assembly 16*a* such inflatable cuff 110 is within the entrance of the anus "An". It is envisioned that the inflatable cuff 110 may instead be received entirely within the anus "An".

Figure 6:
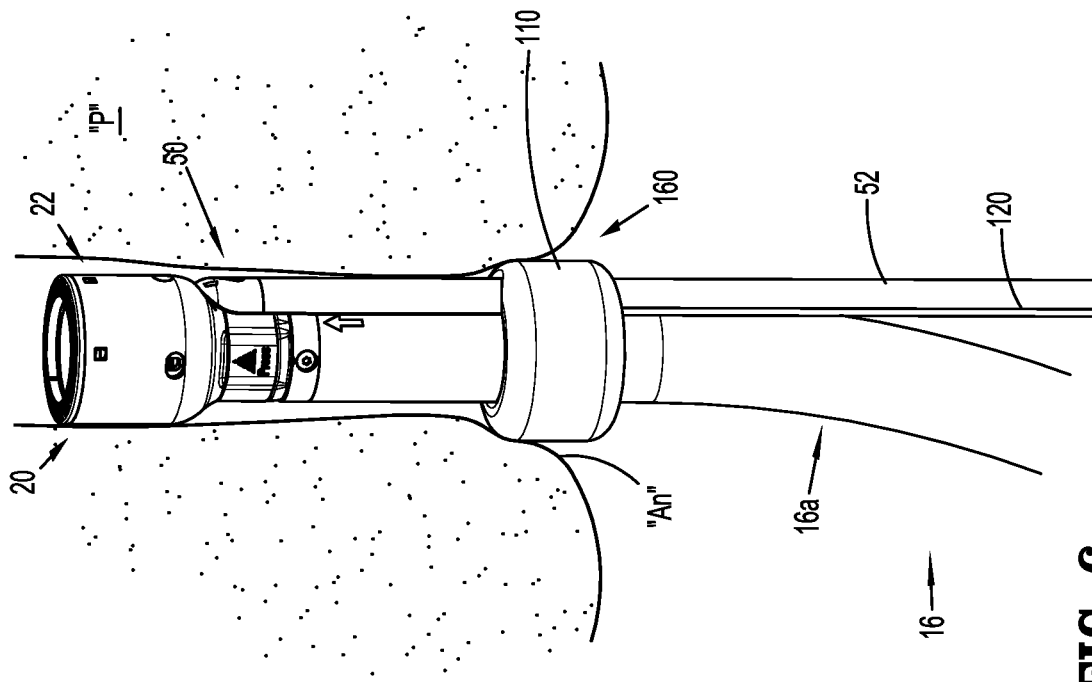
FIG. 6 is a side view of the distal portion of the circular stapling instrument shown in FIG. 5, received within the anus of the patient and with the inflatable cuff in its inflated condition.

FIG. 6 illustrates the inflatable cuff 110 of the seal assembly 100 in the inflated condition. In the inflated condition, the inflatable cuff 110 forms a seal between the tubular body 16*a* of the adapter assembly 16 and the anus "An" of the patient "P". The inflatable cuff 110 may be inflated while in the anus "An" or the inflatable cuff 110 may be inflated and then pressed into the anus "An" by the clinician using the handle assembly 12

It is envisioned that the surgical stapling procedure would be performed prior to the inflating of the inflatable cuff 110 of the seal assembly 100. In this manner, the inflatable cuff 110 of the seal assembly 100 need not be positioned within any particularity along the tubular body 16*a* of the adapter assembly 16.

Once inflated, a leak test is performed as described in the '422 patent to test the integrity of the newly formed anastomosis, or other stapling procedure. The leak test of the anastomosis may be performed without concern for loss of pressure about the tubular body 16*a* of the adapter assembly 16 as the inflatable cuff 110 of the seal assembly 100 prevents any leaks.

Upon completion of the leak test, the inflatable cuff 110 of the seal assembly 100 may be deflated and the end effector 20 of the circular stapling instrument 10 (FIG. 1) removed from the anus "An". It is envisioned that the inflatable cuff 110 may be used as a dilator to facilitate removal of the end effector 20.

The irrigation assembly 50 and the seal assembly 100 may be provided as a part of a kit with a surgical stapling instrument, e.g., circular stapling instrument 10 (FIG. 1).

Figure 7:
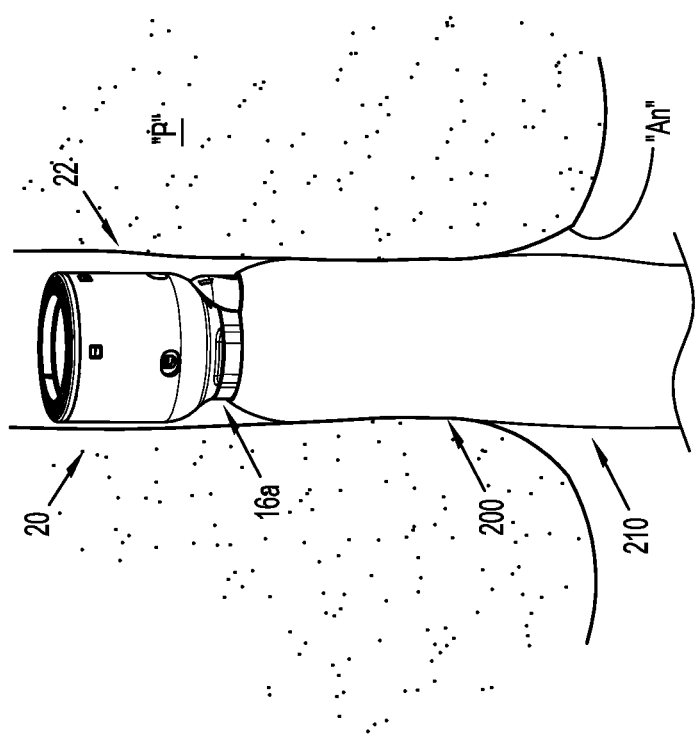
FIG. 7 is a side view of the distal portion of the circular stapling instrument shown in FIG. 1, including seal assembly according to another aspect of the disclosure, received within the anus of the patient and with an inflatable sleeve of the seal assembly in a deflated condition.
Figure 8:
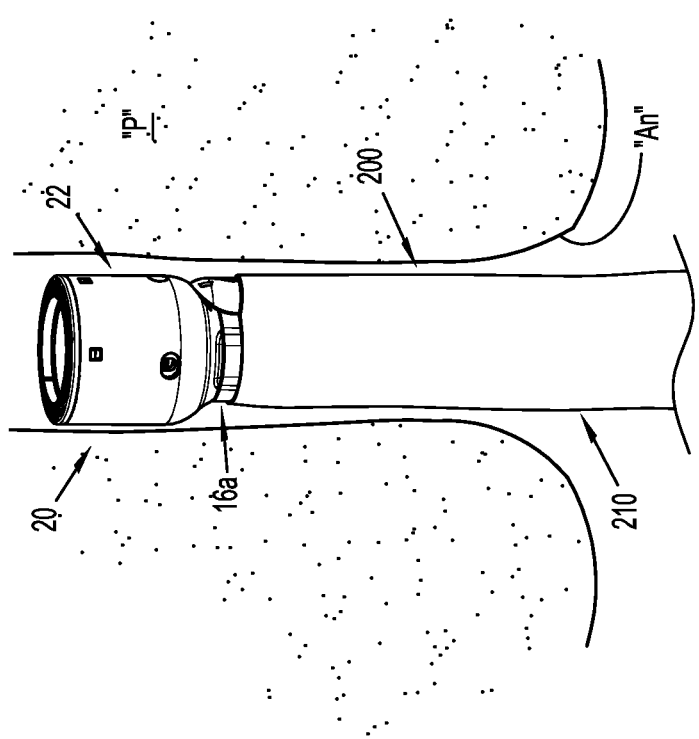
FIG. 8 is a side view of the distal portion of the circular stapling instrument shown in FIG. 7, received within the anus of the patient and with the inflatable sleeve in an inflated condition.

FIGS. 7 and 8 illustrate a seal assembly 200 operably positioned within the anus "An" of a patient. The inflatable sleeve 210 is substantially similar to the inflatable cuff 110 described hereinabove, and therefore will only be described in detail as relates to the differences therebetween.

The seal assembly 200 includes an inflatable sleeve 210. The inflatable sleeve 210 is disposed about the tubular body 16*a* of the adapter assembly 16, and is transitionable between a deflated condition (FIG. 7) and an inflated condition (FIG. 8).

In use, the inflatable sleeve 210 of the seal assembly 200 is inserted within the anus "An" of the patient prior to inflation. In this manner, a clinician does not have to provide any external pressure to the circular stapling instrument 10 (FIG. 1) to ensure a seal between the adapter assembly 16 and the patient "P".

From the foregoing and with reference to the various figure drawings, those skilled in the art will appreciate that certain modifications can also be made to the present surgical stapling instruments without departing from the scope of the same. While several aspects have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope of the claims appended hereto.

What is claimed is:
1. A circular stapling instrument comprising:
   an adapter assembly including a tubular body having a distal portion;
   a shell assembly disposed on the distal portion of the tubular body; and
   a seal assembly supported on the tubular body, the seal assembly including an inflatable member disposed proximal of the shell assembly, wherein the inflatable member includes a first diameter when in a deflated condition and a second diameter when in an inflated condition, the second diameter being larger than the first diameter, wherein the inflatable member is slidably disposed about the tubular body of the adapter assembly when in the deflated condition.

2. The circular stapling instrument of claim 1, wherein the circular stapling instrument further includes an irrigation assembly, the irrigation assembly including a flexible tube.

3. The circular stapling instrument of claim 2, wherein the inflatable member is received about the flexible tube of the irrigation assembly.

4. The circular stapling instrument of claim 1, wherein the seal assembly further includes an inflation tube for providing fluid to the inflatable member.

5. The circular stapling instrument of claim 1, wherein the inflatable member is substantially annular.

6. The circular stapling instrument of claim 1, wherein the inflatable member is an inflatable cuff.

7. The circular stapling instrument of claim 1, wherein the inflatable member is an inflatable sleeve.

8. A circular stapling instrument comprising:
    an adapter assembly including a tubular body having a distal portion;
    a shell assembly disposed on the distal portion of the tubular body; and
    a seal assembly supported on the tubular body, the seal assembly including an inflatable member disposed proximal of the shell assembly, wherein the inflatable member includes a first diameter when in a deflated condition and a second diameter when in an inflated condition, the second diameter being larger than the first diameter, wherein the shell assembly includes a cross-section having a third diameter, the third diameter being greater than the first diameter.

9. The circular stapling instrument of claim 8, wherein the second diameter is greater than the third diameter.

10. The circular stapling instrument of claim 8, wherein the circular stapling instrument further includes an irrigation assembly, the irrigation assembly including a flexible tube.

11. The circular stapling instrument of claim 10, wherein the inflatable member is received about the flexible tube of the irrigation assembly.

12. The circular stapling instrument of claim 8, wherein the seal assembly further includes an inflation tube for providing fluid to the inflatable member.

13. The circular stapling instrument of claim 8, wherein the inflatable member is substantially annular.

14. The circular stapling instrument of claim 8, wherein the inflatable member is an inflatable cuff.

15. The circular stapling instrument of claim 8, wherein the inflatable member is an inflatable sleeve.

16. A method of sealing a tubular body organ to perform a leak test, the method comprising:
    inserting a distal portion of a shell assembly of the circular stapling instrument into an entrance to the tubular body organ;
    performing a stapling procedure; and
    inflating an inflatable member proximal of the shell assembly to create a seal between the distal portion of the circular stapling instrument and the tubular body organ.

17. The method of claim 16, further comprising providing irrigation fluid to the shell assembly.

18. The method of claim 16, further comprising selectively slidably positioning the inflatable member at any location proximal of the shell assembly.

19. The method of claim 16, wherein the inflatable member extends radially about distal portion of the circular stapling instrument.

* * * * *